United States Patent [19]
Taoka et al.

[11] Patent Number: 5,750,382
[45] Date of Patent: May 12, 1998

[54] PROCESS FOR PRODUCING OPTICALLY ACTIVE 2-ALKOXYCYCLOHEXANOL DERIVATIVES

[75] Inventors: Naoaki Taoka; Mizuho Honda, both of Kobe; Kenji Inoue, Kakogawa; Kazunori Kan, Nishinomiya, all of Japan

[73] Assignee: Kaneka Corporation, Osaka, Japan

[21] Appl. No.: 809,431

[22] PCT Filed: Aug. 2, 1996

[86] PCT No.: PCT/JP96/02174

§ 371 Date: Jun. 13, 1997

§ 102(e) Date: Jun. 13, 1997

[87] PCT Pub. No.: WO97/06275

PCT Pub. Date: Feb. 20, 1997

[30] Foreign Application Priority Data

Aug. 4, 1995 [JP] Japan ................................. 7-219728

[51] Int. Cl.$^6$ .............................. C12P 7/62; C12P 41/00; C12N 9/14
[52] U.S. Cl. ................... 435/135; 435/195; 435/196; 435/197; 435/280; 435/829; 435/874; 435/921; 435/931
[58] Field of Search .................................... 435/280, 135, 435/195, 829, 921, 874, 931, 196, 197

[56] References Cited

PUBLICATIONS

Bhattacharya et al "Indian Journal of Chemistry" vol. 31B, Dec. 1991, pp. 898–890.

*Primary Examiner*—Herbert J. Lilling
*Attorney, Agent, or Firm*—Pollock, Vande Sande & Priddy

[57] ABSTRACT

A process for efficiently producing (S,S)-2-alkoxycyclohexanols in a single step by using (±)-trans-2-alkoxycyclohexanols which are inexpensive and can be easily obtained. The process comprises treating a (±)-trans-2-alkoxycyclohexanol with a hydrolase originating in a microorganism and being capable of esterifying stereospecifically the R-isomer in the presence of an acyl donor under such conditions that no hydrolysis occurs substantially to thereby give (S,S)-2-alkoxycyclohexanols and (R,R)-2-alkoxycyclohexanol carboxylate and then taking up the (S,S)-2-alkoxycyclohexanols.

11 Claims, No Drawings

PROCESS FOR PRODUCING OPTICALLY ACTIVE 2-ALKOXYCYCLOHEXANOL DERIVATIVES

BACKGROUND OF THE INVENTION

1. Field of the Invention

The present invention relates to a process for producing an optically active 2-alkoxycyclohexanol derivative, and more particularly, to a process for producing an (S,S)-2-alkoxycyclohexanol.

2. Prior Art

It is known that optically active 2-alkoxycyclohexanol derivatives such as (S,S)-2-alkoxycyclohexanol are important synthetic intermediates in the productions of medicines and agricultural chemicals.

As a process for producing an optically active 2-alkoxycyclohexanol derivative, for example, the following methods have been investigated: ① the process in which a carboxylic ester of a (±)-trans-2-methoxycyclohexanol is hydrolyzed selectively in R-configuration in the presence of hydrolase to give a carboxylic ester of an (S,S)-2-alkoxycyclohexanol and an (R,R)-2-methoxycyclohexanol (Tetrahedron, 50 (35), 10521-30 (1994), Synthesis, 12, 1137-40 (1990), and J. Chem. Soc. Chem. Commun., 3, 148-50 (1989)), ② the process in which a carboxylic ester of a (±)-trans-2-methoxycyclohexanol is hydrolyzed selectively in S-configuration in the presence of hydrolase to give an (S,S)-2-methoxycyclohexanol and a carboxylic ester of an (R,R)-2-alkoxyhexanol (WO94/20634), and ③ the process for obtaining an (R,R)-2-methoxycyclohexanol by asymmetric hydroboration of 1-methoxycyclohexene (J. Org. Chem., 53 (9), 1903-7 (1988)).

Though the process ① is highly stereoselective, the configuration of an optically active 2-alkoxycyclohexanol obtained is (R,R)-configuration and a further hydrolysis of the carboxylic ester of (S,S)-2-alkoxycyclohexanol produced must be carried out in order to obtain (S,S)-2-alkoxycyclohexanol.

Though (S,S)-2-alkoxycyclohexanol can be obtained through the process ②, this method is not sufficiently stereoselective and there are some problems in productive efficiency and economical efficiency.

A stereoselectivity of process ③ is low, and further, there are such problems as reagents used in this process are expensive and etc.

SUMMARY OF THE INVENTION

Taking an account of the above-mentioned circumstances, the object of the present invention is to provide a process for efficiently producing an (S,S)-2-alkoxycyclohexanol in a single step from a (±)-trans-2-alkoxycyclohexanol which is inexpensive and easily available.

The gist of this invention is a process for producing an (S,S)-2-alkoxycyclohexanol which comprises treating a (±)-trans-2-alkoxycyclohexanol which is expressed by the general formula (1);

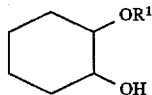
(1)

(wherein $R^1$ represents a lower alkyl, an alkenyl, a cycloalkyl, a substituted or unsubstituted aryl, or a substituted or unsubstituted aralkyl group) with a hydrolase originating in a microorganism which is capable of esterifying the R-isomer stereospecifically in the presence of an acyl donor under a condition that no hydrolysis occurs substantially to thereby give an (S,S)-2-alkoxycyclohexanol which is expressed by the general formula (2);

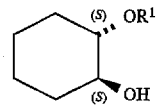
(2)

(wherein $R^1$ is the same as previously defined), and a carboxylic ester of an (R,R)-2-alkoxycyclohexanol which is expressed by the general formula (3)

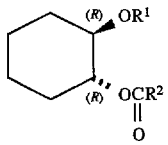
(3)

(wherein $R^1$ is the same as previously defined and $R^2$ represents a hydrogen, straight-chain or branched alkyl having 1 to 17 carbon atoms, or straight-chain or branched alkenyl group having 1 to 17 carbon atoms), and then taking up said (S,S)-2-alkoxycyclohexanol.

DETAILED DESCRIPTION OF THE INVENTION

Hereinafter, the present invention is explained in more details.

A (±)-trans-2-alkoxycyclohexanol which is used in this invention is a compound given in the above general formula (1). $R^1$ in the above formula is not specially limited to but includes a lower alkyl group such as methyl, ethyl, propyl, isopropyl, n-butyl, isobutyl, t-butyl, sec-butyl and the like; an alkenyl group such as vinyl, allyl, isobutenyl and the like; a cycloalkyl group such as cyclohexyl, cyclopentyl and the like; a substituted or unsubstituted aryl group such as p-nitrophenyl, a phenyl and the like; and a substituted or unsubstituted aralkyl group such as p-nitrobenzyl, benzyl and the like. Among these, a methyl group is preferable.

The above (±)-trans-2-alkoxycyclohexanol can be synthesized easily from cyclohexene oxide which can be obtained commercially, and a corresponding alcohol, for example, by the method which proposed in J. Am. Chem. Soc., 65, 2196 (1943).

Preferable examples of an acyl donor which is used in the present invention can be either compounds expressed by a general formula (4);

$$(R^2CO)_2O \qquad (4)$$

(wherein $R^2$ represents a hydrogen atom, straight-chain or branched alkyl having 1 to 17 carbon atoms, or straight-chain or branched alkenyl group having 1 to 17 carbon atoms), compounds expressed by a general formula (5);

$$R^3OOCR^2 \qquad (5)$$

(wherein $R^2$ is the same as previously defined, $R^3$ is a straight-chain or branched alkyl having 1 to 17 carbon atoms, straight-chain or branched alkenyl group having 2 to 17 carbon atoms, 2,2,2-trihalogenoethyl group, or a substituted or unsubstituted phenyl), or compounds expressed by a general formula (6);

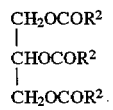

(wherein R² is the same as previously defined).

R² mentioned above is not particularly limited to but includes a hydrogen; an alkyl group such as methyl, ethyl, propyl, isopropyl, n-butyl, isobutyl, t-butyl, sec-butyl, pentyl, heptyl and the like; and an alkenyl group such as vinyl, allyl, isopropenyl, isobutenyl and the like. Among these, a propyl group is preferable.

R³ mentioned above is not particularly limited to but includes an alkyl group such as methyl, ethyl, propyl, isopropyl, n-butyl, isobutyl, t-butyl, sec-butyl and the like; an alkenyl group such as vinyl, isopropenyl and the like; a trihalogenoethyl group such as 2,2,2-trichloroethyl, 2,2,2-tribromoethyl, 2,2,2-trifluoroethyl and the like; and a substituted or unsubstituted aryl group such as p-nitrophenyl, phenyl and the like. Among these, a vinyl group is preferable.

The above acyl donor preferably includes butyric anhydride, vinyl butyrate, tributyrin and so on.

The hydrolase originating in a microorganism which is capable of esterifying the R-isomer stereospecifically, which is used in the present invention, is not particularly limited to but includes lipase, esterase, acylase, and so on.

Preferable are a lipase derived from microorganisms which belong to Alkaligenes, a lipase derived from microorganisms which belong to Candida, a lipase derived from microorganisms which belong to Pseudomonas, a lipase derived from microorganisms which belong to Mucor, and the like.

The above lipase derived from microorganisms which belong to Alkaligenes includes "Lipase PL" (a registered trademark of product of MEITO SANGYO Co.) and so on. The above lipase derived from microorganisms which belong to Candida includes "Novozym 435" (a registered trademark of product of Novo-Nordisk A/S), "Lipase OF" (a registered trademark of product of MEITO SANGYO Co.), "Lipase MY" (a registered trademark of product of MEITO SANGYO Co.) and so on. The above lipase derived from microorganisms which belong to Pseudomonas includes "Lipase PS AMANO" (a registered trademark of product of AMANO PHARMACEUTICAL Co.) and so on. The above lipase derived from microorganisms which belong to Mucor includes "Lipozyme IM" (a registered trademark of product of Novo-Nordisk A/S).

The above hydrolase originating in microorganisms which is capable of esterifying the R-isomer stereospecifically can also be used in the form of microorganisms cells containing said hydrolase. The example of the above microorganism cells includes a yeast which belongs to Alkaligenes, Candida, Pseudomonas, Mucor and etc. and cells such as filamentous fungi, bacteria and so on.

In the present invention, the above microorganism cells can be used in any treatment cells forms such as freeze-dried cells, cells treated by acetone, toluene and so on, cell homogenate, an extract from cells and so on.

The above microorganism cells and treatment cells can be used as they are, or after immobilized.

The producing process for an optically active 2-alkoxycyclohexanol derivative in the present invention can be carried out, for example, as follows.

A (±)-trans-2-alkoxycyclohexanol as a stating material is dissolved in a solvent in the concentration of 0.1 to 70 w/v %, preferably 1 to 50 w/v %, and there are added 0.5 to 10 times equivalent, preferably 0.5 to 2 times equivalent of above-mentioned acyl donor to the (±)-trans-2-alkoxycyclohexanol and 0.001 to 10 parts by weight, preferably 0.01 to 1 parts by weight of the above-mentioned hydrolase which is capable of esterifying the R-isomer stereospecifically to the (±)-trans-2-alkoxycyclohexanol, and the solution was mixed under stirring to carry out asymmetric esterification.

After completion of the asymmetric esterification, the hydrolase described above is recovered by filtration or centrifugation as insoluble material. Purified (S,S)-2-alkoxycyclohexanol and purified carboxylic ester of (R,R)-2-alkoxycyclohexanol are obtained by concentration and distillation of the filtrate.

In the present invention, the asymmetric esterification described above is carried out under the condition where no hydrolysis reaction occurs substantially. For example, because hydrolysis which is reverse reaction of an above esterification proceeds in the case of the presence of water in the system, it is preferable that above-described asymmetric esterification is performed in the solvent that contains no water or a very little amount of water.

The solvent used in the present invention is not particularly limited to but includes solvents which do not inactivate the hydrolase, for example, a hydrocarbon type solvents such as toluene, hexane and so on; ether type solvents such as diisopropyl ether, tetrahydrofuran, methyl tert-butyl ether and so on; ketone type solvents such as acetone and methyl ethyl ketone; and ester type solvents such as ethyl butyrate.

In the present invention, the above asymmetric esterification can be carried out without the above solvent except the above substrate and the reaction reagent.

The reaction temperature in the process of the above asymmetric esterification is preferably 0° C. to 80° C., and more preferably 10° C. to 50° C.

The reaction time in the process of the above asymmetric esterification is preferably 1 to 240 hours, and more preferably 1 to 72 hours.

BEST MODE FOR CARRYING OUT THE INVENTION

The invention will be described in more detail with reference to the following example, which are not intended to restrict the scope of the invention.

EXAMPLES 1 to 6

The mixture of 260 mg of (±)-trans-2-methoxycyclohexanol, 1.27 ml of vinyl butyrate and 130 mg of various kinds of lipase was poured in 15 ml-screw tubes and a reaction was carried out for 24 hours at room temperature during agitating. The resulted reaction mixture was filtered. The conversion rate was determined by GC analysis of the filtrate. From the residual trans-2-methoxycyclohexanol, a derivative thereof was given (DNB derivative), and the optical purity was measured by HPLC analysis. Every configuration of the trans-2-methoxycyclohexanol was (S,S)-configuration. The conversion rate and the optical purity are shown in table 1.

EXAMPLES 7 to 30

After 130 mg of (±)-trans-2-methoxycyclohexanol and 127 µl of vinyl butyrate were poured in 15 ml-screw tubes, dissolved in 1 ml of various kind of solvent, and there was added 65 mg of various kind of lipase. The mixture was reacted at 30° C. for 24 hours during stirring. The solution was filtered and the conversion rate was determined by GC analysis of the filtrate. From the residual trans-2-methoxycyclohexanol, a derivative thereof was given (DNB derivative), and the optical purity was measured by HPLC analysis. Every configuration of the trans-2-methoxycyclohexanol was (S,S)-configuration. The conversion rate and the optical purity are shown in table 2.

EXAMPLES 31 to 54

After 130 mg of (±)-trans-2-methoxycyclohexanol and 127 μl of various kind of acyl donor were poured in 15 ml-screw tubes, dissolved in 1 ml of toluene, and there was added 65 mg of various kind of lipase. The mixture was reacted at 30° C. for 24 to 96 hours during stirring. The solution was filtered and the conversion rate was determined by GC analysis of the filtrate. From the residual trans-2-methoxycyclohexanol, a derivative thereof was given (DNB derivative), and the optical purity was measured by HPLC.

Every configuration of the trans-2-methoxycyclohexanol was (S,S)-configuration. The conversion rate and the optical purity are shown in table 3.

TABLE 1

| Example | Enzyme for use | Conversion rate (%) | Optical purity (% ee) |
| --- | --- | --- | --- |
| 1 | Lipase PL (Alkaligenes origin, MEITO SANGYO Co.) | 54.9 | 21.4 |
| 2 | Novozym 435 (Candida origin, Novo-Nordisk A/S) | 51.5 | 100 |
| 3 | Lipase OF (Candida origin, MEITO SANGYO Co.) | 48.7 | 79 |
| 4 | Lipase MY (Candida origin, MEITO SANGYO Co.) | 22.1 | 21.4 |
| 5 | Lipase PS AMANO (Pseudomonas origin, AMANO PHARMACEUTICALS Co.) | 47.7 | 94.8 |
| 6 | Lipozyme IM (Mucor origin, Novo-Nordisk A/S) | 51.2 | 100 |

TABLE 2

| Example | Enzyme for use | Reaction solvent | Conversion rate (%) | Optical purity (% ee) |
| --- | --- | --- | --- | --- |
| 7 | Novozym 435 (Candida origin, Novo-Nordisk A/S) | Hexane | 57.8 | 96.6 |
| 8 | Novozym 435 (Candida origin, Novo-Nordisk A/S) | Toluene | 52.6 | 98.7 |
| 9 | Novozym 435 (Candida origin, Novo-Nordisk A/S) | Diisopropyl ether | 54.6 | 95.7 |
| 10 | Novozym 435 (Candida origin, Novo-Nordisk A/S) | Tetrahydrofuran | 51.4 | 97.8 |
| 11 | Novozym 435 (Candida origin, Novo-Nordisk A/s) | Methyl tert-butyl ether | 53.8 | 93.3 |
| 12 | Novozym 435 (Candida origin, Novo-Nordisk A/S) | Acetone | 41.8 | 77.7 |
| 13 | Novozym 435 (Candida origin, Novo-Nordisk A/S) | Methyl ethyl ketone | 53.3 | 98.7 |
| 14 | Novozym 435 (Candida origin, Novo-Nordisk A/S) | Ethyl butyrate | 53.5 | 98.9 |
| 15 | Lipase PS AMANO (Pseudomonas origin, AMANO PHARMACEUTICALS Co.) | Hexane | 50.3 | 95.9 |
| 16 | Lipase PS AMANO (Pseudomonas origin, AMANO PHARMACEUTICALS Co.) | Toluene | 51.8 | 100 |
| 17 | Lipase PS AMANO (Pseudomonas origin, AMANO PHARMACEUTICALS Co.) | Diisopropyl ether | 52.4 | 100 |
| 18 | Lipase PS AMANO (Pseudomonas origin, AMANO PHARMACEUTICALS Co.) | Tetrahydrofuran | 51.5 | 98.2 |
| 19 | Lipase PS AMANO (Pseudomonas origin, AMANG PHARMACEUTICALS Co.) | Methyl tert-butyl ether | 52.6 | 100 |
| 20 | Lipase PS AMANO (Pseudomonas origin, AMANO PHARMACEUTICALS Co.) | Acetone | 50.7 | 100 |
| 21 | Lipase PS AMANO (Pseudomonas origin, AMANO PHARMACEUTICALS Co.) | Methyl ethyl ketone | 44 | 77.5 |
| 22 | Lipase PS AMkNO (Pseudomonas origin, AMAND PHARMACEUTICALS Co.) | Ethyl butyrate | 50.3 | 95.9 |
| 23 | Lipozyme IM (Mucor origin, Novo-Nordisk A/S) | Hexane | 49.3 | 87.8 |
| 24 | Lipozyme IM (Mucor origin, Novo-Nordisk A/S) | Toluene | 51.9 | 100 |
| 25 | Lipozyme IM (Mucor origin, Novo-Nordisk A/S) | Diisopropyl ether | 51.5 | 95.8 |
| 26 | Lipozyme IM (Mucor origin, Novo-Nordisk A/S) | Tetrahydrofuran | 42.4 | 76.2 |
| 27 | Lipozyme IM (Mucor origin, Novo-Nordisk A/S) | Methyl tert-butyl ether | 52.1 | 95.3 |
| 28 | Lipozyme IM (Mucor origin, Novo-Nordisk A/S) | Acetone | 26.6 | 49.3 |
| 29 | Lipozyme IM (Mucor origin, Novo-Nordisk A/S) | Methyl ethyl ketone | 44.7 | 82.3 |
| 30 | Lipozyme IM (Mucor origin, Novo-Nordisk A/S) | Ethyl butyrate | 46.9 | 84.8 |

TABLE 3

| Example | Enzyme for use | Acyl donor | Conversion rate (%) | Optical purity (% ee) |
| --- | --- | --- | --- | --- |
| 31 | Novozym 435 (Candida origin, Novo-Nordisk A/S) | Acetic anhydride | 31.9 | 54.8 |
| 32 | Novozym 435 (Candida origin, Novo-Nordisk A/S) | Vinyl acetate | 48.4 | 86.3 |
| 33 | Novozym 435 (Candida origin, Novo-Nordisk A/S) | Isopropenyl acetate | 52.6 | 95.6 |
| 34 | Novozym 435 (Candida origin, Novo-Nordisk A/S) | Butyric anhydride | 49.1 | 96.2 |
| 35 | Novozym 435 (Candida origin, Novo-Nordisk A/S) | Vinyl butyrate | 57.1 | 95.9 |
| 36 | Novozym 435 (Candida origin, Novo-Nordisk A/S) | Tributyrin | 38.3 | 57.9 |
| 37 | Novozym 435 (Candida origin, Novo-Nordisk A/S) | Ethyl butyrate | 30.7 | 44.6 |
| 38 | Novozym 435 (Candida origin1 Novo-Nordisk A/S) | Vinyl capronate | 51.5 | 95.9 |
| 39 | Lipase PS AMANO (Pseudomonas origin, AMANO PHARMACEUTICALS Co.) | Acetic anhydride | 46.1 | 81.8 |
| 40 | Lipase PS AMANO (Pseudomonas origin, AMANO PHARMACEUTICALS Co.) | Vinyl acetate | 40.7 | 73.8 |

TABLE 3-continued

| Example | Enzyme for use | Acyl donor | Conversion rate (%) | Optical purity (% ee) |
|---|---|---|---|---|
| 41 | Lipase PS AMANO (Pseudomonas origin, AMANO PHARMACEUTICALS Co.) | Isopropenyl acetate | 15. 8 | — |
| 42 | Lipase PS AMANO (Pseudomonas origin, AMANG PHARMACEUTICALS Co.) | Butyric anhydride | 15.2 | — |
| 43 | Lipase PS AMANO (Pseudomonas origin, AMANO PHRAMACEUTICALS Co.) | Vinyl butyrate | 51.9 | 95.8 |
| 44 | Lipase PS AMANO (Pseudomonas origin, AMANO PHARMACEUTICALS Co.) | Tributyrin | 24.2 | — |
| 45 | Lipase PS AMANO (Pseudomonas origin, AMANO PHARMACEUTICALS Co.) | Ethyl butyrate | 15.5 | — |
| 46 | Lipase PS AMANO (Pseudomonas origin, AMANO PHARMACEUTICALS Co.) | Vinyl capronate | 54.8 | 94.9 |
| 47 | Lipozyme IM (Mucor origin, Novo-Nordisk A/S) | Acetic anhydride | 17.2 | — |
| 48 | Lipozyme IM (Mucor origin, Novo-Nordisk A/S) | Vinyl acetate | 46.3 | 87.3 |
| 49 | Lipozyme IM (Mucor origin, Nevo-Nordisk A/S) | Isopropenyl acetate | 35.8 | 64.4 |
| 50 | Lipozyme IM (Mucor origin, Novo-Nordisk A/S) | Butyric anhydride | 40.1 | 64.1 |
| 51 | Lipozyme IM (Mucor origin, Novo-Nordisk A/S) | Vinyl butyrate | 52.3 | 96 |
| 52 | Lipozyme IM (Mucor origin, Novo-Nordisk A/S) | Tributyrin | 34.8 | 53.8 |
| 53 | Lipozyme IM (Mucor origin, Novo-Nordisk A/S) | Ethyl butyrate | 23.2 | — |
| 54 | Lipozyme IM (Mucor origin, NovO-Nordisk A/S) | Vinyl capronate | 54.8 | 95.7 |

Industrial Applicability

Because of the above-mentioned constitute according to the present invention, we can produce an (S,S)-2-alkoxycyclohexanol efficiently and easily, which are useful for intermediates on production of medicines.

We claim:

1. A process for producing an optically active 2-alkoxycyclohexanol derivative which comprises treating a (±)-trans-2-alkoxycyclohexanol which is expressed by the general formula (1);

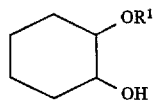
(1)

(wherein $R^1$ represents a lower alkyl, an alkenyl, a cycloalkyl, a substituted or unsubstituted aryl, or a substituted or unsubstituted aralkyl group) with a hydrolase originating in a microorganism which is capable of esterifying the R-isomer stereospecifically, in the presence of an acyl donor under a condition that no hydrolysis occurs substantially, to thereby give an (S,S)-2-alkoxycyclohexanol which is expressed by the general formula (2);

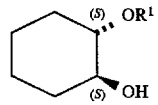
(2)

(wherein $R^1$ is the same as previously defined), and a carboxylic ester of an (R,R)-2-alkoxycyclohexanol which is expressed by the general formula (3);

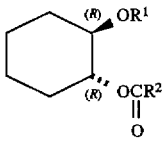
(3)

(wherein $R^1$ is the same as previously defined and $R^2$ represents a hydrogen, straight-chain or branched alkyl having 1 to 17 carbon atoms, or straight-chain or branched alkenyl group having 1 to 17 carbon atoms), and then taking up said (S,S)-2-alkoxycyclohexanol.

2. The process for producing an optically active 2-alkoxycyclohexanol derivative according to claim 1 wherein said (±)-trans-2-alkoxycyclohexanol is (±)-trans-2-methoxycyclohexanol.

3. The process for producing an optically active 2-alkoxycyclohexanol derivative according to claim 1 wherein the acyl donor is a compound expressed by the following formula (4);

$$(R^2CO)_2O \qquad (4)$$

(wherein $R^2$ represents a hydrogen atom, straight-chain or branched alkyl having 1 to 17 carbon atoms, or straight-chain or branched alkenyl group having 2 to 17 carbon atoms), a compound expressed by the following formula (5);

$$R^3OOCR^2 \qquad (5)$$

(wherein $R^2$ is the same as previously defined, and $R^3$ represents straight-chain or branched alkyl having 1 to 17 carbon atoms, straight-chain or branched alkenyl group having 2 to 17 carbon atoms, 2,2,2-trihalogenoethyl group, or a substituted or unsubstituted phenyl), or a compound expressed by the following formula (6);

(6)

(wherein $R^2$ is the same as previously defined).

4. The process for producing an optically active 2-alkoxycyclohexanol derivative according to claim 1 wherein the acyl donor is butyric anhydride, vinyl butyrate or tributyrin.

5. The process for producing an optically active 2-alkoxycyclohexanol derivative according to claim 1 or 4 wherein said hydrolase originating in a microorganism which is capable of esterifying the R-isomer stereospecifically is a lipase derived from microorganisms which belong to Alkaligenes, a lipase derived from microorganisms which belong to Candida, a lipase derived from microorganisms which belong to Pseudomonas or a lipase derived from microorganisms which belong to Mucor.

6. The process for producing an optically active 2-alkoxycyclohexanol derivative according to claim 2 wherein the acyl donor is a compound expressed by the following fomula (4);

$$(R^2CO)_2O \qquad (4)$$

(wherein $R^2$ represents a hydrogen atom, straight-chain or branched alkyl having 1 to 17 carbon atoms, or straight-chain or branched alkenyl group having 2 to 17 carbon atoms), a compound expressed by the following formula (5);

$$R^3OOCR^2 \quad (5)$$

(wherein $R^2$ is the same as previously defined, and $R^3$ represents straight-chain or branched alkyl having 1 to 17 carbon atoms, straight-chain or branched alkenyl group having 2 to 17 carbon atoms, 2,2,2-trihalogenoethyl group, or a substituted or unsubstituted phenyl), or a compound expressed by the following formula (6)

$$\begin{array}{l} CH_2OCR^2 \\ | \\ CHOCOR^2 \\ | \\ CH_2OCOR^2 \end{array} \quad (6)$$

(wherein $R^2$ is the same as previously defined).

7. The process for producing an optically active 2-alkoxycyclohexanol derivative according to claim 2 wherein the acyl donor is butyric anhydride, vinyl butyrate or tributyrin.

8. The process for producing an optically active 2-alkoxycyclohexanol derivative according to claim 3 wherein the acyl donor is butyric anhydride, vinyl butyrate or tributyrin.

9. The process for producing an optically active 2-alkoxycyclohexanol derivative according to claim 2 wherein said hydrolase originating in a microorganism which is capable of esterifying the R-isomer stereospecifically is a lipase derived from microorganisms which belong to Alkaligenes, a lipase derived from microorganisms which belong to Candida, a lipase derived from microorganisms which belong to Pseudomonas or a lipase derived from microorganisms which belong to Mucor.

10. The process for producing an optically active 2-alkoxycyclohexanol derivative according to claim 3 wherein said hydrolase originating in a microorganism which is capable of esterifying the R-isomer stereospecifically is a lipase derived from microorganisms which belong to Alkaligenes, a lipase derived from microorganisms which belong to Candida, a lipase derived from microorganisms which belong to Pseudomonas or a lipase derived from microorganisms which belong to Mucor.

11. The process for producing an optically active 2-alkoxycyclohexanol derivative according to claim 4 wherein said hydrolase originating in a microorganism which is capable of esterifying the R-isomer stereospecifically is a lipase derived from microorganisms which belong to Alkaligenes, a lipase derived from microorganisms which belong to Candida, a lipase derived from microorganisms which belong to Pseudomonas or a lipase derived from microorganisms which belong to Mucor.

* * * * *